United States Patent [19]

Harson

[11] 4,234,496

[45] Nov. 18, 1980

[54] COMPLEX ORGANO-METALLIC COMPOUNDS OF BORON OR PHOSPHORUS

[75] Inventor: Samuel E. Harson, Warrington, England

[73] Assignee: Manchem Limited, Manchester, England

[21] Appl. No.: 41,418

[22] Filed: May 22, 1979

[30] Foreign Application Priority Data

May 26, 1978 [GB] United Kingdom ............... 23007/78

[51] Int. Cl.$^3$ ............................ A23J 7/00; C07F 9/02; C11C 3/00
[52] U.S. Cl. .................................. 260/403; 260/438.1; 260/429.3; 260/439 R; 260/414; 106/245; 106/268
[58] Field of Search .................. 260/403, 438.1, 429.3, 260/439 R, 414; 106/245, 268

[56] References Cited

U.S. PATENT DOCUMENTS

| | | | |
|---|---|---|---|
| 2,777,776 | 1/1957 | Kieras | 106/272 |
| 3,321,426 | 5/1967 | Dorsey | 106/272 |
| 3,467,683 | 9/1969 | Harson et al. | 260/403 |
| 3,661,607 | 5/1972 | Hurley | 106/272 |

FOREIGN PATENT DOCUMENTS 972804 10/1964 United Kingdom .

*Primary Examiner*—John F. Niebling
*Attorney, Agent, or Firm*—James R. Thornton

[57] ABSTRACT

Compounds comprising three atoms of a divalent metal linked through oxygen atoms to an atom selected from the group consisting of a boron atom, a phosphorus atom and a phosphorus atom bonded to an oxo oxygen, and an aliphatic monocarboxylic acid radical attached to each divalent metal atom, at least one of said aliphatic monocarboxylic acid radicals having from 7 to 9 carbon atoms, and at least one other of said aliphatic monocarboxylic acid radicals having 10 or 11 carbon atoms, and the polymerization products thereof, are useful as rubber compound adhesion promoters and are more easily handled than the previously known compounds and polymers used for this purpose.

12 Claims, No Drawings

COMPLEX ORGANO-METALLIC COMPOUNDS OF BORON OR PHOSPHORUS

FIELD OF THE INVENTION

This invention relates to complex metal organic compounds and compositions containing the element boron or phosphorus and to methods of preparing the compounds and compositions.

DESCRIPTION OF THE PRIOR ART

Metal organic compounds containing boron or phosphorus have been previously described. For example, U.K. Pat. Specification No. 1,075,125 discloses compounds comprising one or more divalent metals linked through oxygen atoms to a phosphorus atom or atoms, one carboxylic acid radical attached to a divalent metal atom or one or more carboxylic acid radicals attached to the divalent metals when more than one metal is used, and, in some cases, one or more alkoxy groups or aryloxy groups attached to the phosphorus atom or atoms. These compounds are useful for example as paint driers, lubricant and oil additives and stabilisers, particularly for PVC. The general appearances of the products can vary from oily liquids to waxy and sticky solids at room temperature. It should be noted that compounds falling within the scope of the above patent which are prepared from the now no longer available Versatic 911 acid ("Versatic" is a Trade Mark), a mixture of cyclic and tertiary acids containing 9–11 carbon atoms, are always hard and brittle solids which form great quantities of dust when broken up.

U.K. Pat. Specification No. 972,804 discloses compounds which contain aluminium or boron, at least one divalent metal element or metal radical, the aluminium or boron atom and divalent atoms being linked through oxygen atoms, and at least one carboxylic acid radical. These compounds vary in form from oily liquids to waxy, resinous or amorphous solids and in many cases the products have good solubility in or compatibility with hydrocarbon or ester type media or with certain polar products such as P.V.C. for which they are effective heat stabilisers and processing aids.

In many applications there are advantages in using the products described above in the form of discrete particles such as granules, pastilles or flakes. Powders containing up to substantially 70% by weight of active ingredient dispersed on an inert carrier have been proposed but these are not completely satisfactory. The physical properties of the previously known products do not allow their manufacture as large particles so hitherto they have mainly been used in solution in organic solvents. A particular application of the products is as additives for rubber mixtures to improve the adhesion of rubber compound to metallic surfaces such as steel, brass and zinc plate substrates, which is important in the manufacture of rubber tires for example. The use of the products in their liquid form creates handling problems, and because of this, liquid formulations are not well liked in the tyre manufacturing industry.

One major area of application of these compounds, in particular those containing cobalt, is in the manufacture of motor vehicle tires. Where these contain steel or brass-plated or zinc-plated wire reinforcement, such compounds promote adhesion between the wire reinforcement and the rubber body of the tire. The materials presently used for this purpose have disadvantages which this invention sets out to overcome.

The compounds in present use are essentially solid materials which are added to the rubber formulations either as the solid or as liquids obtained by dissolving the solid in a suitable solvent. To achieve the desired properties in the finished tire it is essential that these substances be added to the rubber formulation in precisely determined amounts. Where the solid forms of these materials is preferred, the physical nature of the solid causes difficulties in both the safe handling of the material and its accurate dispensation into the rubber mix. The former point is of particular significance at a time of increasing awareness of the potential health hazard posed by compounds containing heavy metals, while the latter is of obvious importance to the tire manufacturer.

An example of the problems encountered in the handling of such compounds is provided by reference to cobalt naphthenate, widely used as an adhesion promoter by the tire industry. This material has the disadvantage that its physical form can vary from a soft, sticky semi-solid to a hard, brittle product depending on the nature of the naphtheric acid used in its manufacture. Uncertainty over the supply of naphtheric acid, which is an oil-based product, has meant that producers of cobalt naphtherate have been unable to guarantee a consistent product. Whatever the physical form of the product its use presents the tire manufacturers with certain problems. In its soft form, it is particularly difficult to obtain exactly the required amount for addition to the rubber mix. In its hard form, the material forms substantial amounts of dust when lumps are crushed prior to addition to the rubber mix. This dust constitutes a health hazard to those handling the material.

To overcome these disadvantages, it is proposed to supply solid materials in the form of free-flowing powders on non-agglomerating granules, pastilles or flakes as required.

SUMMARY OF THE INVENTION

We have sought to provide complex metal organic compounds containing the element boron or phosphorus which are substantially tack-free solids at room temperature and which may be converted into free-flowing powders or non-agglomerating granules, pastilles or flakes as required, and used as rubber adhesion promoters, without the disadvantages of having to use solutions thereof.

To achieve these desired properties, the solid products must not be so brittle as to fracture during normal handling procedures as would the products of U.K. Pat. No. 1,075,125, thereby causing the formation of undesirable particles of dust. This is particularly important in the manufacture of products by flaking processes. Further the granules of the like of these materials should be free flowing up to temperatures of substantially 50° C. which temperatures may be reached on storage in metal containers in ware houses under hot climatic conditions.

DETAILED DESCRIPTION

According to a first aspect of the present invention, there is provided compounds comprising three atoms of a divalent metal linked through oxygen atoms to an atom selected from the group consisting of boron atom a phosphorus atom and a phosphorous atom having an oxo oxygen bonded thereto, and an aliphatic monocarboxylic acid radical having from 7 to 11 carbon atoms attached to each divalent metal atom, at least one of said aliphatic monocarboxylic acid radicals having from 7 to 9 carbon atoms, and at least one other of said monocarboxylic acid radicals having 10 or 11 carbon atoms.

According to a second aspect of the invention we provide compounds of the formula:

$$Q(OMA_xB_yC_z)_3 \text{ or } PO(OMA_xB_yC_z)_3$$

wherein Q represents phosphorus or boron; M represents a divalent metal; A, B and C represent aliphatic monocarboxylate groups, with the proviso that at least one group contains 7–9 carbon atoms and at least one group contains 10–11 carbon atoms, and at most two only of A, B and C can be identical; and x, y and z are each independently greater than zero with $x+y+z=1$.

According to a third aspect of the present invention there is provided compounds of the formula:

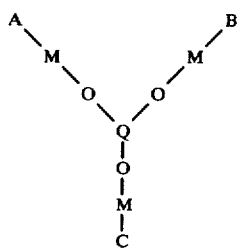
(1)

wherein M represents a divalent metal Q is an atom selected from the group consisting of a boron atom, a phosphorous atom and a phosphorous atom having an oxo oxygen bonded thereto and X, Y and Z represent monocarboxylate groups containing 7–11 carbon atoms with the provisos that at least one of X, Y and Z contains 7–9 carbon atoms, and at least one other of X, Y and Z contains 10 or 11 carbon atoms.

According to a fourth aspect of the invention, we provide compositions comprising a compound of the formula (1) as defined above and a compound of the general formula B-(OMA')$_3$ or PO(OMA')$_3$ wherein M is as defined above and A' is an aliphatic monocarboxylate group containing 7–11 carbon atoms.

It is a feature of this invention that the compounds or compositions manufactured according to the processes described herein may contain polymerisation products of the compounds which are thought to be produced by transesterification during the reaction processes.

The compounds and compositions of the invention are substantially tack-free solids at room temperature. On heating, they begin to soften above 50° C. and at higher temperatures become free-flowing liquids which may be converted into dustless, free-flowing powders or larger, non-agglomerating particles by conventional processes such as prilling, spray cooling, shower-cooling, pastillating and drum flaking. The compounds and compositions of the present invention may have their physical properties improved by the incorporation therein of microcrystalline waxes.

The compounds and compositions of the invention are generally prepared by the reaction at an elevated temperature of a mixed carboxylic acid metal salt with an organo-boron or organo-phosphorus compound as defined herein and the subsequent removal of the volatile ester by-product. The mixed carboxylic acid metal salts are generally prepared from a divalent metal or from a divalent metal compound such as the hydrate, hydroxide or carbonate. The metal or metal compound is treated for example with a mixture comprising two appropriate carboxylic acids containing 7–11 carbon atoms and an approximately equimolar amount of acetic or propionic acid. When the reaction mixture is viscous, an organic solvent may be added to thin the reaction mixture and to aid dissolution. Preferred solvents are hydrocarbons such as white spirit and xylene. Acetic acid is usually preferred to propionic acid except in the cases where the divalent metal acetates are insoluble in the hydrocarbon solvents employed.

The following sets out examples of relevant $C_7$–$C_{11}$ aliphatic monocarboxylate acids:

$C_7$
n-heptanoic
2,2-dimethylpentanoic
2-ethylpentanoic
4,4-dimethylpentanoic $C_8$
n-octanoic
2,2-dimethylhexanoic
2-ethylhexanoic
4,4-dimethylhexanoic
2,4,4-trimethylpentanoic $C_9$
n-nonanoic
2,2-dimethylheptanoic
6,6-dimethylheptanoic
3,5,5-trimethylhexanoic $C_{10}$
n-decanoic
2,2-dimethyloctanoic
7,7-dimethyloctanoic $C_{11}$
n-undecanoic
"Versatic" 10 (trade mark), a synthetic acid mixture which is mainly neodecanoic acid, and is marketed in the U.K. by Shell International Company Limited. "Cekanoic" (trade mark), i.e. a class of acids which are mixtures of isomers containing 8–10 carbon atoms and which may be represented by the formula:

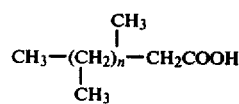

where $n = 3-5$

The preferred divalent metals are cobalt and manganese but other metals that may be used include barium, calcium, cerium, copper, iron, magnesium, nickel, strontium zirconium and the like. In any case, any metal which can exist in a divalent state may be used.

Boron may be used in the form of alkyl or aryl orthoborates such as n- butyl orthoborate or metaborates. This element is most conveniently used in the form of an alkoxide derived from a volatile alcohol containing up to four carbon atoms, the preferred alkoxides being the iso-butoxide and n-butoxide of boron.

Phosphorus may be used in the form of alkyl or aryl phosphates or phosphites, or of acid alkyl phosphates or phosphites. The preferred phosphorus compounds are the mono-, di-, tri- or higher esters of orthophosphoric acid, poly-phosphoric acids or phosphorous acids. Typical examples are tributyl phosphate, mixed butyl phosphoric acid, isobutyl phosphoric acids, triethyl phosphate acid butyl phosphate and dibutyl phosphate.

The invention is further illustrated by reference to the following examples:

EXAMPLE 1

Cobalt hydrate (3 mols) was dissolved in a mixture of "versatic" 10 (2 mols), isononanoic acid (1 mol) and acetic acid (3.15 mols). Water formedduring the reaction was removed by heating the mixture to a temperature of 190° C. over a period of four hours. The mixed acid soap thus produced was reacted with n-butyl orthoborate (1 mol) and the displaced acetic acid was distilled off as butyl acetate by heating the reactants to a temperature of 235° C. over a period of six hours.

When cool, the product consisted of a dark blue, hard, substantially tack-free solid.

EXAMPLE 2

Cobalt hydrate (3 mols) was dissolved in a mixture of "Versatic" 10 (2 mols), 2-ethylhexanoic acid (1 mol) and acetic acid (3.15 mols). Water formed during the reaction was removed by heating the mixture to a temperature of 180° C. over a period of 4½ hours. The mixture acid soap thus, produced was reacted with n-butyl orthoborate (1 mol) and the displaced acetic acid was distilled off as butyl acetate by heating the reactants to a temperature of 230° C. over a period of five hours.

When cool, the product consisted of a dark blue, substantially tack-free solid.

EXAMPLE 3

Cobalt metal was dissolved in a mixture of "Versatic" 10 (2 mols) isononanoic acid (1 mol) and propionic acid (3.07 mols), by circulating a solution of the mixed acids in a hydrocarbon solvent at an elevated temperature through a bed of cobalt metal particles. Reaction was continued until the required concentration of cobalt in the solution was obtained (ca 10% w/v). The hydrocarbon solvent was removed by vacuum distillation and the cobalt soap reacted with n-butyl orthoborate (1 mol) as in Example 2. The product consisted of a hard, dark blue, substantially tack-free solid containing 23.2 wt.% cobalt.

EXAMPLE 4

Cobalt hydrate (3 mols) was dissolved in a mixture of "Versatic" 10 (2 mols), isononanoic acid (1 mol) and propionic acid (3 mols), the water of reaction being removed by distillation to a temperature of 194° C. The cobalt soap was allowed to cool to 130° C. and reacted with a mixed acid butyl phosphate (1 mol). Volatile esters were removed from the reaction mixture by vacuum distillation at 220° C. On cooling, the product was obtained as a hard substantially tack-free solid.

EXAMPLE 5

The solid product as formed in Example 1 was converted into the form of a fine, dust-free powder consisting of spherical particles having a controlled particle size distribution. The process was carried out by atomising a stream of the molten product by means of a spinning disc.

The product formed as described in Example 1 was heated to 180° C. at which temperature it was a mobile liquid having a viscosity of about 2 poises. A stream of this liquid was allowed to impinge on the centre of a horizontal rotating disc (diameter 25 cms.) rotating at 2200 r.p.m. This caused the liquid film which formed to break up into spherical droplets having a mean diameter of about 200 microns. The droplets were allowed to harden before being collected in a cyclone and bag-filter arrangement.

EXAMPLE 6

The solid product as formed in Example 2 was collected in the form of small pastilles having a diameter of 6 mm and a thickness of 2 mm. This was achieved by means of an arrangement whereby small drops of the molten material at a temperature of 180° C. were placed on a water-cooled moving steel belt. The length of the belt and its rate of movement were such that the discrete drops were allowed to cool and to harden before being removed by a mechanical scraper.

EXAMPLE 7

The solid product of Example 1 was conveniently converted into a thin sheet (approximately 1-2 mm thick) on a conventional drum flaker at a temperature of 140° C. The sheet was allowed to harden whereupon it readily broke up into irregularly shaped pieces whose size was governed by the thickness of the sheet and the nature of the handling procedure adopted.

This process has the advantage that more viscous materials can be handled, thereby permitting the use of lower temperatures.

EXAMPLE 8

Manganous oxide (3 mols) was dissolved in a mixture of "Versatic" 10 (2 mols), 3,5,5-trimethyl hexanoic acid (1 mol) and propionic acid (3 mols). Water of reaction was removed by heating to a temperature of 213° C. under vacuum. The reactants were cooled to 190° C. and n-butylorthoborate (1 mol) added. Burtyl propionate was distilled from the reactor, final traces being removed by applying vacuum at a temperature of 230° C. The product when cool was a hard, dark brown solid.

EXAMPLE 9

Iron powder (3 mols) was dissolved in a mixture of 2-ethyl hexanoic acid (1.5 mols), "Versatic" 10 (1.5 mols), and pripionic acid (3.1 mols) in a hydrocarbon solvent. Solution was effected by heating the reactions until no further hydrogen was evolved and then n-butyl orthoborate (1 mol) was added. Butyl propionate was distilled from the system along with the hydrocarbon solvent, final traces being removed by heating the product to a temperature of 240° C. When cool, the product was a hard, dark-brown solid.

EXAMPLE 10

Cobalt hydrate (3 mols) was dissolved in a mixture of "Versatic" 10 (1 mol), 2-ethyl hexanoic acid (1 mol), 3,5,5-trimethylhexanoic acid (1 mol) and acetic acid (3.15 mols). Water of reaction was removed by heating the reactants to 190° C. for 3 hours. n-butylorthoborate (1 mol) was then added and butyl acetate distilled from the mixture. Final traces of butyl ester were removed by heating under vacuum to 240° C. When cool, the product was a hard, dark-blue solid.

EXAMPLE 11

Manganous oxide (3 mols) was dissolved in a mixture of Cekanoic acid (1.5 mols), 2-ethyl hexanoic acid (1.5 mols) and propionic acid (3.1 mols). The resultant soap was dried by heating to 220° C. under vacuum and the product cooled to 180° C. n-butylorthoborate (1 mol)

was added and the mixture heated to distil off butyl propionate. The reaction was completed by heating to 240° C. under vacuum to give a product which, when cool, was a hard, dark-brown solid.

EXAMPLE 12

Nickel hydrate (3 mols) was dissolved in a mixture of "Versatic" 10 (1 mol), 2-ethyl hexanoic acid (2 mols) and acetic acid (3.1 mols). The water of reaction was removed by heating to 200° C. for four hours. The reactants were cooled and n-butylorthoborate (1 mol) added. Butyl acetate was distilled from the system to give a product which, on cooling, was a hard, dark-green solid.

EXAMPLE 13

Cobalt hydrate (3 mols) was dissolved in a mixture of "Versatic" 10 (1 mol), 2-ethyl hexanoic acid (1 mol), isononanoic acid (1 mol) and acetic acid (3.15 mols). Water formed during the reaction was removed by heating the mixture to a temperature of 190° C. over a period of 4 hours. The mixed acid soap thus produced was reacted with n-butyl orthoborate (1 mol) and the displaced acetic acid distilled off as butyl acetate by heating the reactants to a temperature of 235° C. over a period of 5½ hours. The cooled product consisted of a dark-blue, tack-free solid.

EXAMPLE 14

Cobalt metal was dissolved in a mixture of "Versatic" 10 (1.5 mols) 2-ethyl hexanoic acid (1 mol), isononanoic acid (0.5 mol) and propionic acid (3.15 mols), by circulating a solution of the mixed acids in white spirit at an elevated temperature through a bed of cobalt metal particles. Reaction was continued until the concentration of cobalt in solution had reached 10% w/v. The solvent was removed by vacuum distillation and the cobalt soap was reacted with n-butyl orthoborate (1 mol) and the propionic acid was distilled off as butyl propionate by heating the reactants to a temperature of 230° C. over a period of five hours.

The product consisted of a dark blue, tack free solid containing 23.8% by weight cobalt.

EXAMPLE 15

Cobalt was dissolved in a mixture of "Versatic" 10 (2 mols), isononanoic acid (1 mol) and propionic acid (3.07 mol) by circulating a solution of the mixed acids in white spirit at an elevated temperature through a bed of cobalt metal particles. The dissolution procedure was continued until the solution contained about 10% w/v cobalt. The hydrocarbon solvent was removed by vacuum distillation and the cobalt soap was reacted with n-butyl orthoborate (1 mol). The propionic acid was distilled off as butyl propionate by heating the reactants to a temperature of 230° C. over a period of 5 hours. When distillation was completed and before cooling the product Shell Micro Wax 185/190 was added in an amount which would represent 5% w/w of the final product. The wax was thoroughly mixed and the composition allowed to cool.

The composition could be formed into pastilles as described in Example 7.

What is claimed is:

1. Solid compounds comprising three atoms of a divalent metal selected from the group consisting of iron, cobalt, and manganese, linked through oxygen atoms to an atom selected from the group consisting of a boron atom and a phosphorus atom having an oxo oxygen bonded thereto, and a monocarboxylic acid bonded thereto, and a monocarboxylic acid radical having 7 to 11 carbon atoms attached to each divalent metal atom, at least one of said monocarboxylic acid radicals having from 7 to 9 carbon atoms, and at least one other of said monocarboxylic radicals having 10 or 11 carbon atoms.

2. Solid compounds of the formula:

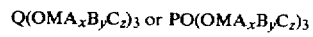

wherein Q represents phosphorus or boron; M represents a divalent metal selected from the group consisting of iron, cobalt and manganese; A, B and C represent aliphatic monocarboxylate groups, with the proviso that at least one group contains 7–9 carbon atoms and at least one group contains 10–11 carbon atoms, and at most two only of A, B and C can be identical; and x, y and z are each independently greater than zero with $x+y+z=1$.

3. Solid compounds of formula:

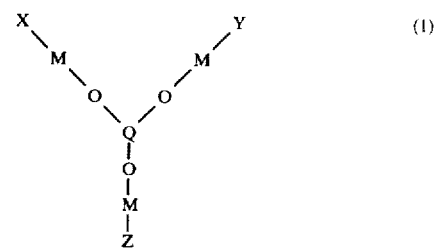

wherein M is a divalent metal selected from the group consisting of iron, cobalt and manganese, Q is an atom selected from the group consisting of a boron atom, a phosphorus atom or a phosphorus atom having an oxo oxygen bonded thereto, and X, Y and Z represent monocarboxylic acid groups containing 7–11 carbon atoms with the proviso that at least one of X, Y and Z contains 7–9 carbon atoms, and at least one other of X, Y and Z contains 10–11 carbon atoms.

4. Compounds as claimed in claim 1 wherein the divalent metal is cobalt.

5. A composition which comprises a solid compound as claimed in claim 1 and a compound of the general formula:

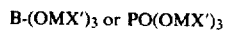

wherein M is selected from the group consisting of iron, cobalt and manganese and X' is a monocarboxylate group containing 7 to 11 carbon atoms.

6. A compound as claimed in claim 1 in combination with one or more microcrystalline waxes.

7. A composition as claimed in claim 5 in combination with one or more microcrystalline waxes.

8. A process for the preparation of a solid compound as claimed in claim 1 which comprises reacting an appropriately substituted mixed carboxylic acid salt of a divalent metal selected from the group consisting of iron, cobalt and manganese with a compound selected from the group consisting of an alkyl orthoborate, aryl orthoborate, an alkyl metaborate, an aryl metaborate, an alkyl phosphate, an aryl phosphate, an alkyl phosphite, an aryl phosphite, an acid alkyl phosphate and an acid alkyl phosphite, at an elevated temperature.

9. A process as claimed in claim 8 wherein the divalent carboxylic acid metal salt is prepared by treating the divalent metal or a salt thereof with a mixture of carboxylic acids containing 7-11 carbon atoms and an acid selected from the group consisting of acetic propionic acid.

10. A process as claimed in claim 8 wherein the divalent metal is cobalt.

11. Compounds as claimed in claim 1 wherein the divalent metal is iron.

12. Compounds as claimed in claim 1 wherein the divalent metal is manganese.

* * * * *